United States Patent
Kobayashi et al.

(10) Patent No.: US 10,590,497 B2
(45) Date of Patent: Mar. 17, 2020

(54) TRICHODERMA FUNGUS HAVING MUTANT-TYPE BXL1 GENE AND METHOD OF PRODUCING XYLOOLIGOSACCHARIDE AND GLUCOSE BY USING SAME

(71) Applicant: Toray Industries, Inc., Tokyo (JP)

(72) Inventors: Koji Kobayashi, Kamakura (JP); Shingo Hiramatsu, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/089,271

(22) PCT Filed: Mar. 30, 2017

(86) PCT No.: PCT/JP2017/013379
§ 371 (c)(1),
(2) Date: Sep. 27, 2018

(87) PCT Pub. No.: WO2017/170918
PCT Pub. Date: Oct. 5, 2017

(65) Prior Publication Data
US 2019/0055614 A1 Feb. 21, 2019

(30) Foreign Application Priority Data
Mar. 31, 2016 (JP) .................... 2016-070690

(51) Int. Cl.
| | |
|---|---|
| C13K 1/02 | (2006.01) |
| C12N 1/14 | (2006.01) |
| C12N 15/01 | (2006.01) |
| C13K 13/00 | (2006.01) |
| C12N 15/09 | (2006.01) |
| C12N 9/24 | (2006.01) |
| C12P 19/04 | (2006.01) |
| C12P 19/14 | (2006.01) |
| C12R 1/885 | (2006.01) |

(52) U.S. Cl.
CPC .............. *C12R 1/885* (2013.01); *C12N 1/14* (2013.01); *C12N 9/2402* (2013.01); *C12N 15/01* (2013.01); *C12N 15/09* (2013.01); *C12P 19/04* (2013.01); *C12P 19/14* (2013.01); *C13K 1/02* (2013.01); *C13K 13/00* (2013.01); *C12Y 302/01037* (2013.01)

(58) Field of Classification Search
None
See application file for complete search history.

(56) References Cited

U.S. PATENT DOCUMENTS

| | | |
|---|---|---|
| 6,177,261 B1 | 1/2001 | De Graaff et al. |
| 2009/0062232 A1 | 3/2009 | Fujikawa et al. |
| 2013/0143277 A1 | 6/2013 | Gutierrez et al. |
| 2016/0326559 A1 | 11/2016 | Funada et al. |
| 2017/0314051 A1 | 11/2017 | Yamada et al. |

FOREIGN PATENT DOCUMENTS

| | | |
|---|---|---|
| JP | 11-507837 A | 7/1999 |
| JP | 2009-171885 A | 8/2009 |
| JP | 4675139 B2 | 4/2011 |
| JP | 2013-515482 A | 5/2013 |
| WO | 2014/208493 A1 | 12/2014 |
| WO | 2015/099109 A1 | 7/2015 |
| WO | 2016/068223 A1 | 5/2016 |
| WO | 2016/100825 A1 | 6/2016 |

OTHER PUBLICATIONS

Aachary, A. A. et al., "Xylooligosaccharides (XOS) as an Emerging Prebiotic: Microbial Synthesis, Utilization, Structural Characterization, Bioactive Properties, and Applications," *Comprehensive Reviews in Food Science and Food Safety*, 2011, vol. 10, pp. 2-16.

Moniz, P. et al., "Hydrothermal production and gel filtration purification of xylo-oligosaccharides from rice straw," *Industrial Crops and Products*, 2014, vol. 62, pp. 460-465.

Akpinar, O. et al., "Production of xylooligosaccharides by controlled acid hydrolysis of lignocellulosic materials," *Carbohydrate Research*, 2009, vol. 344, Issue 5, pp. 660-666, Abstract only.

Herrmann, M. C. et al., "The β-d-xylosidase of Trichoderma reesei is a multifunctional β-d-xylan xylohydrolase," *Biochemical Journal*, 1997, vol. 321, No. 2, pp. 375-381, Abstract only.

"Glycoside Hydrolase Family 3," *Carbohydrate-Active EnZYmes Database*, (http://www.cazy.org/GH3.html).

Rasmussen, L. E. et al., "Mode of action and properties of the β-xylosidases from *Talaromyces emersonii* and *Trichoderma reesei*," *Biotechnol. Bioeng.*, 2006, vol. 94, No. 5, pp. 869-876, Abstract only.

Margolles-Clark, E. et al., "Cloning of Genes Encoding α-L-Arabinofuranosidase and β-Xylosidase from *Trichoderma reesei* by Expression in *Saccharomyces cerevisiae*," *Applied and Environmental Microbiology*, 1996, vol. 62, No. 10, pp. 3840-3846.

Mao, L. S. et al., "Study on Production of Xylo-oligosaccharides from Xylan Hydrolyzed by Selectively Purified Endo-β-xylanase," *Linchan Huaxue Yu Gongye*, 2006, vol. 26, No. 1, pp. 124-126, Abstract only.

*Primary Examiner* — Suzanne M Noakes
*Assistant Examiner* — Jae W Lee
(74) *Attorney, Agent, or Firm* — DLA Piper LLP (US)

(57) ABSTRACT

A novel fungus belongs to the genus *Trichoderma* whose cellulase can be used to hydrolyze cellulose-based biomass without degradation of xylan contained in the biomass into xylose, and a method produces glucose and xylo-oligosaccharides from a cellulose containing biomass using it. The fungus belonging to the genus *Trichoderma* includes N- and C-terminal domains of the β-xylosidase 1 (BXL1) gene, but lacks the Fn3-like domain of the gene due to its disruption. The use of this fungus belonging to the genus *Trichoderma* results in deletion of β-xylosidase activity and increase in β-glucosidase activity. Thus, in hydrolysis of cellulose contained in biomass, xylan contained in the biomass is not degraded into xylose, which enables efficient production of glucose and xylo-oligosaccharides.

19 Claims, 1 Drawing Sheet

Specification includes a Sequence Listing.

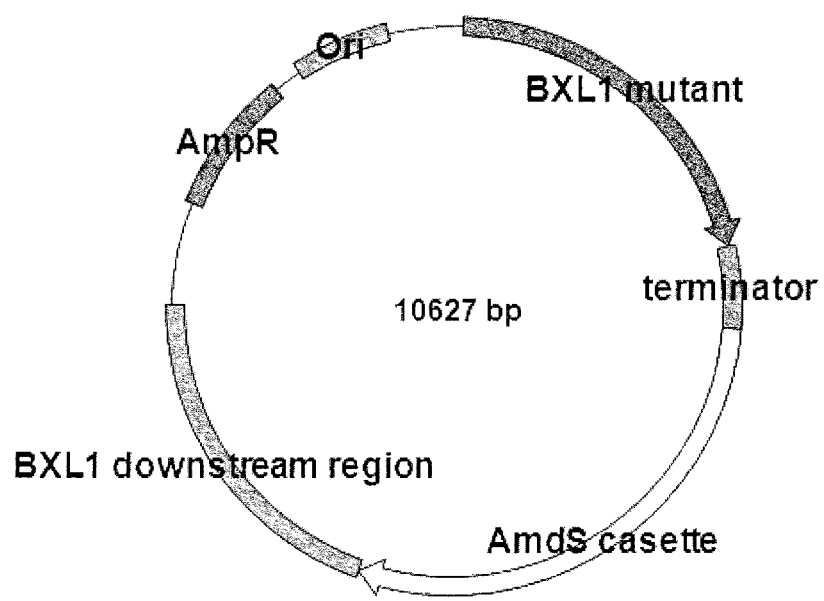

US 10,590,497 B2

SEQUENCE LISTING

<160> NUMBER OF SEQ ID NOS: 8

<210> SEQ ID NO 1
<211> LENGTH: 2394
<212> TYPE: DNA
<213> ORGANISM: Trichoderma reesei
<220> FEATURE:
<221> NAME/KEY: CDS
<222> LOCATION: (1)..(2394)

<400> SEQUENCE: 1

```
atg gtg aat aac gca gct ctt ctc gcc gcc ctg tcg gct ctc ctg ccc     48
Met Val Asn Asn Ala Ala Leu Leu Ala Ala Leu Ser Ala Leu Leu Pro
1               5                   10                  15 acg gcc ctg gcg cag aac aat caa aca tac gcc aac tac tct gct cag     96
Thr Ala Leu Ala Gln Asn Asn Gln Thr Tyr Ala Asn Tyr Ser Ala Gln
            20                  25                  30 ggc cag cct gat ctc tac ccc gag aca ctt gcc acg ctc aca ctc tcg    144
Gly Gln Pro Asp Leu Tyr Pro Glu Thr Leu Ala Thr Leu Thr Leu Ser
        35                  40                  45 ttc ccc gac tgc gaa cat ggc ccc ctc aag aac aat ctc gtc tgt gac    192
Phe Pro Asp Cys Glu His Gly Pro Leu Lys Asn Asn Leu Val Cys Asp
    50                  55                  60 tca tcg gcc ggc tat gta gag cga gcc cag gcc ctc atc tcg ctc ttc    240
Ser Ser Ala Gly Tyr Val Glu Arg Ala Gln Ala Leu Ile Ser Leu Phe
65                  70                  75                  80 acc ctc gag gag ctc att ctc aac acg caa aac tcg ggc ccc ggc gtg    288
Thr Leu Glu Glu Leu Ile Leu Asn Thr Gln Asn Ser Gly Pro Gly Val
                85                  90                  95 cct cgc ctg ggt ctt ccg aac tac caa gtc tgg aat gag gct ctg cac    336
Pro Arg Leu Gly Leu Pro Asn Tyr Gln Val Trp Asn Glu Ala Leu His
            100                 105                 110 ggc ttg gac cgc gcc aac ttc gcc acc aag ggc ggc cag ttc gaa tgg    384
Gly Leu Asp Arg Ala Asn Phe Ala Thr Lys Gly Gly Gln Phe Glu Trp
        115                 120                 125 gcg acc tcg ttc ccc atg ccc atc ctc act acg gcg gcc ctc aac cgc    432
Ala Thr Ser Phe Pro Met Pro Ile Leu Thr Thr Ala Ala Leu Asn Arg
    130                 135                 140 aca ttg atc cac cag att gcc gac atc atc tcg acc caa gct cga gca    480
Thr Leu Ile His Gln Ile Ala Asp Ile Ile Ser Thr Gln Ala Arg Ala
```

-continued

| | | | | |
|---|---|---|---|---|
| 145 | 150 | 155 | 160 | |
| ttc agc aac agc ggc cgt tac ggt ctc gac gtc tat gcg cca aac gtc<br>Phe Ser Asn Ser Gly Arg Tyr Gly Leu Asp Val Tyr Ala Pro Asn Val<br>               165                  170                175 | | | | 528 |
| aat ggc ttc cga agc ccc ctc tgg ggc cgt ggc cag gag acg ccc ggc<br>Asn Gly Phe Arg Ser Pro Leu Trp Gly Arg Gly Gln Glu Thr Pro Gly<br>          180                185               190 | | | | 576 |
| gaa gac gcc ttt ttc ctc agc tcc gcc tat act tac gag tac atc acg<br>Glu Asp Ala Phe Phe Leu Ser Ser Ala Tyr Thr Tyr Glu Tyr Ile Thr<br>              195                200             205 | | | | 624 |
| ggc atc cag ggt ggc gtc gac cct gag cac ctc aag gtt gcc gcc acg<br>Gly Ile Gln Gly Gly Val Asp Pro Glu His Leu Lys Val Ala Ala Thr<br>210                215                220 | | | | 672 |
| gtg aag cac ttt gcc gga tac gac ctc gag aac tgg aac aac cag tcc<br>Val Lys His Phe Ala Gly Tyr Asp Leu Glu Asn Trp Asn Asn Gln Ser<br>225              230              235            240 | | | | 720 |
| cgt ctc ggt ttc gac gcc atc ata act cag cag gac ctc tcc gaa tac<br>Arg Leu Gly Phe Asp Ala Ile Ile Thr Gln Gln Asp Leu Ser Glu Tyr<br>                245              250             255 | | | | 768 |
| tac act ccc cag ttc ctc gct gcg gcc cgt tat gca aag tca cgc agc<br>Tyr Thr Pro Gln Phe Leu Ala Ala Ala Arg Tyr Ala Lys Ser Arg Ser<br>          260                265              270 | | | | 816 |
| ttg atg tgc gca tac aac tcc gtc aac ggc gtg ccc agc tgt gcc aac<br>Leu Met Cys Ala Tyr Asn Ser Val Asn Gly Val Pro Ser Cys Ala Asn<br>              275                280             285 | | | | 864 |
| agc ttc ttc ctg cag acg ctt ttg cgc gag agc tgg ggc ttc ccc gaa<br>Ser Phe Phe Leu Gln Thr Leu Leu Arg Glu Ser Trp Gly Phe Pro Glu<br>290              295                300 | | | | 912 |
| tgg gga tac gtc tcg tcc gat tgc gat gcc gtc tac aac gtt ttc aac<br>Trp Gly Tyr Val Ser Ser Asp Cys Asp Ala Val Tyr Asn Val Phe Asn<br>305              310              315            320 | | | | 960 |
| cct cat gac tac gcc agc aac cag tcg tca gcc gcc gcc agc tca ctg<br>Pro His Asp Tyr Ala Ser Asn Gln Ser Ser Ala Ala Ala Ser Ser Leu<br>              325              330             335 | | | | 1008 |
| cga gcc ggc acc gat atc gac tgc ggt cag act tac ccg tgg cac ctc<br>Arg Ala Gly Thr Asp Ile Asp Cys Gly Gln Thr Tyr Pro Trp His Leu<br>          340                345              350 | | | | 1056 |
| aac gag tcc ttt gtg gcc ggc gaa gtc tcc cgc ggc gag atc gag cgg<br>Asn Glu Ser Phe Val Ala Gly Glu Val Ser Arg Gly Glu Ile Glu Arg<br>              355              360             365 | | | | 1104 |
| tcc gtc acc cgt ctg tac gcc aac ctc gtc cgt ctc gga tac ttc gac<br>Ser Val Thr Arg Leu Tyr Ala Asn Leu Val Arg Leu Gly Tyr Phe Asp<br>          370                375              380 | | | | 1152 |
| aag aag aac cag tac cgc tcg ctc ggt tgg aag gat gtc gtc aag act<br>Lys Lys Asn Gln Tyr Arg Ser Leu Gly Trp Lys Asp Val Val Lys Thr<br>385              390              395            400 | | | | 1200 |
| gat gcc tgg aac atc tcg tac gag gct gct gtt gag ggc atc gtc ctg<br>Asp Ala Trp Asn Ile Ser Tyr Glu Ala Ala Val Glu Gly Ile Val Leu<br>              405              410             415 | | | | 1248 |
| ctc aag aac gat ggc act ctc cct ctg tcc aag aag gtg cgc agc att<br>Leu Lys Asn Asp Gly Thr Leu Pro Leu Ser Lys Lys Val Arg Ser Ile<br>          420                425              430 | | | | 1296 |
| gct ctg atc gga cca tgg gcc aat gcc aca acc caa atg caa ggc aac<br>Ala Leu Ile Gly Pro Trp Ala Asn Ala Thr Thr Gln Met Gln Gly Asn<br>              435              440             445 | | | | 1344 |
| tac tat ggc cct gcc cca tac ctc atc agc cct ctg gaa gct gct aag<br>Tyr Tyr Gly Pro Ala Pro Tyr Leu Ile Ser Pro Leu Glu Ala Ala Lys<br>450              455              460 | | | | 1392 |
| aag gcc ggc tat cac gtc aac ttt gaa ctc ggc aca gag atc gcc ggc | | | | 1440 |

```
Lys Ala Gly Tyr His Val Asn Phe Glu Leu Gly Thr Glu Ile Ala Gly
465                 470                 475                 480 aac agc acc act ggc ttt gcc aag gcc att gct gcc gcc aag aag tcg      1488
Asn Ser Thr Thr Gly Phe Ala Lys Ala Ile Ala Ala Ala Lys Lys Ser
                485                 490                 495 gat gcc atc atc tac ctc ggt gga att gac aac acc att gaa cag gag      1536
Asp Ala Ile Ile Tyr Leu Gly Gly Ile Asp Asn Thr Ile Glu Gln Glu
                500                 505                 510 ggc gct gac cgc acg gac att gct tgg ccc ggt aat cag ctg gat ctc      1584
Gly Ala Asp Arg Thr Asp Ile Ala Trp Pro Gly Asn Gln Leu Asp Leu
                515                 520                 525 atc aag cag ctc agc gag gtc ggc aaa ccc ctt gtc gtc ctg caa atg      1632
Ile Lys Gln Leu Ser Glu Val Gly Lys Pro Leu Val Val Leu Gln Met
530                 535                 540 ggc ggt ggt cag gta gac tca tcc tcg ctc aag agc aac aag aag gtc      1680
Gly Gly Gly Gln Val Asp Ser Ser Ser Leu Lys Ser Asn Lys Lys Val
545                 550                 555                 560 aac tcc ctc gtc tgg ggc gga tat ccc ggc cag tcg gga ggc gtt gcc      1728
Asn Ser Leu Val Trp Gly Gly Tyr Pro Gly Gln Ser Gly Gly Val Ala
                565                 570                 575 ctc ttc gac att ctc tct ggc aag cgt gct cct gcc ggc cga ctg gtc      1776
Leu Phe Asp Ile Leu Ser Gly Lys Arg Ala Pro Ala Gly Arg Leu Val
                580                 585                 590 acc act cag tac ccg gct gag tat gtt cac caa ttc ccc cag aat gac      1824
Thr Thr Gln Tyr Pro Ala Glu Tyr Val His Gln Phe Pro Gln Asn Asp
                595                 600                 605 atg aac ctc cga ccc gat gga aag tca aac cct gga cag act tac atc      1872
Met Asn Leu Arg Pro Asp Gly Lys Ser Asn Pro Gly Gln Thr Tyr Ile
610                 615                 620 tgg tac acc ggc aaa ccc gtc tac gag ttt ggc agt ggt ctc ttc tac      1920
Trp Tyr Thr Gly Lys Pro Val Tyr Glu Phe Gly Ser Gly Leu Phe Tyr
625                 630                 635                 640 acc acc ttc aag gag act ctc gcc agc cac ccc aag agc ctc aag ttc      1968
Thr Thr Phe Lys Glu Thr Leu Ala Ser His Pro Lys Ser Leu Lys Phe
                645                 650                 655 aac acc tca tcg atc ctc tct gct cct cac ccc gga tac act tac agc      2016
Asn Thr Ser Ser Ile Leu Ser Ala Pro His Pro Gly Tyr Thr Tyr Ser
                660                 665                 670 gag cag att ccc gtc ttc acc ttc gag gcc aac atc aag aac tcg ggc      2064
Glu Gln Ile Pro Val Phe Thr Phe Glu Ala Asn Ile Lys Asn Ser Gly
                675                 680                 685 aag acg gag tcc cca tat acg gcc atg ctg ttt gtt cgc aca agc aac      2112
Lys Thr Glu Ser Pro Tyr Thr Ala Met Leu Phe Val Arg Thr Ser Asn
690                 695                 700 gct ggc cca gcc ccg tac ccg aac aag tgg ctc gtc gga ttc gac cga      2160
Ala Gly Pro Ala Pro Tyr Pro Asn Lys Trp Leu Val Gly Phe Asp Arg
705                 710                 715                 720 ctt gcc gac atc aag cct ggt cac tct tcc aag ctc agc atc ccc atc      2208
Leu Ala Asp Ile Lys Pro Gly His Ser Ser Lys Leu Ser Ile Pro Ile
                725                 730                 735 cct gtc agt gct ctc gcc cgt gtt gat tct cac gga aac cgg att gta      2256
Pro Val Ser Ala Leu Ala Arg Val Asp Ser His Gly Asn Arg Ile Val
                740                 745                 750 tac ccc ggc aag tat gag cta gcc ttg aac acc gac gag tct gtg aag      2304
Tyr Pro Gly Lys Tyr Glu Leu Ala Leu Asn Thr Asp Glu Ser Val Lys
                755                 760                 765 ctt gag ttt gag ttg gtg gga gaa gag gta acg att gag aac tgg ccg      2352
Leu Glu Phe Glu Leu Val Gly Glu Glu Val Thr Ile Glu Asn Trp Pro
770                 775                 780
```

```
ttg gag gag caa cag atc aag gat gct aca cct gac gca taa        2394
Leu Glu Glu Gln Gln Ile Lys Asp Ala Thr Pro Asp Ala
785                 790                 795
```

<210> SEQ ID NO 2
<211> LENGTH: 797
<212> TYPE: PRT
<213> ORGANISM: Trichoderma reesei

<400> SEQUENCE: 2

```
Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
```

```
              355                 360                 365
Ser Val Thr Arg Leu Tyr Ala Asn Leu Val Arg Leu Gly Tyr Phe Asp
370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
                420                 425                 430

Ala Leu Ile Gly Pro Trp Ala Asn Ala Thr Thr Gln Met Gln Gly Asn
                435                 440                 445

Tyr Tyr Gly Pro Ala Pro Tyr Leu Ile Ser Pro Leu Glu Ala Ala Lys
            450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Lys Lys Ser
                485                 490                 495

Asp Ala Ile Ile Tyr Leu Gly Gly Ile Asp Asn Thr Ile Glu Gln Glu
                500                 505                 510

Gly Ala Asp Arg Thr Asp Ile Ala Trp Pro Gly Asn Gln Leu Asp Leu
                515                 520                 525

Ile Lys Gln Leu Ser Glu Val Gly Lys Pro Leu Val Val Leu Gln Met
530                 535                 540

Gly Gly Gly Gln Val Asp Ser Ser Leu Lys Ser Asn Lys Lys Val
545                 550                 555                 560

Asn Ser Leu Val Trp Gly Gly Tyr Pro Gly Gln Ser Gly Gly Val Ala
                565                 570                 575

Leu Phe Asp Ile Leu Ser Gly Lys Arg Ala Pro Ala Gly Arg Leu Val
                580                 585                 590

Thr Thr Gln Tyr Pro Ala Glu Tyr Val His Gln Phe Pro Gln Asn Asp
                595                 600                 605

Met Asn Leu Arg Pro Asp Gly Lys Ser Asn Pro Gly Gln Thr Tyr Ile
            610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
                660                 665                 670

Glu Gln Ile Pro Val Phe Thr Phe Glu Ala Asn Ile Lys Asn Ser Gly
                675                 680                 685

Lys Thr Glu Ser Pro Tyr Thr Ala Met Leu Phe Val Arg Thr Ser Asn
                690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
                740                 745                 750

Tyr Pro Gly Lys Tyr Glu Leu Ala Leu Asn Thr Asp Glu Ser Val Lys
            755                 760                 765

Leu Glu Phe Glu Leu Val Gly Glu Glu Val Thr Ile Glu Asn Trp Pro
770                 775                 780
```

```
Leu Glu Glu Gln Gln Ile Lys Asp Ala Thr Pro Asp Ala
785                 790                 795
```

<210> SEQ ID NO 3
<211> LENGTH: 2232
<212> TYPE: DNA
<213> ORGANISM: Trichoderma reesei
<220> FEATURE:
<221> NAME/KEY: CDS
<222> LOCATION: (1)..(2232)

<400> SEQUENCE: 3

```
atg gtg aat aac gca gct ctt ctc gcc gcc ctg tcg gct ctc ctg ccc        48
Met Val Asn Asn Ala Ala Leu Leu Ala Ala Leu Ser Ala Leu Leu Pro
1               5                   10                  15 acg gcc ctg gcg cag aac aat caa aca tac gcc aac tac tct gct cag        96
Thr Ala Leu Ala Gln Asn Asn Gln Thr Tyr Ala Asn Tyr Ser Ala Gln
                20                  25                  30 ggc cag cct gat ctc tac ccc gag aca ctt gcc acg ctc aca ctc tcg       144
Gly Gln Pro Asp Leu Tyr Pro Glu Thr Leu Ala Thr Leu Thr Leu Ser
            35                  40                  45 ttc ccc gac tgc gaa cat ggc ccc ctc aag aac aat ctc gtc tgt gac       192
Phe Pro Asp Cys Glu His Gly Pro Leu Lys Asn Asn Leu Val Cys Asp
        50                  55                  60 tca tcg gcc ggc tat gta gag cga gcc cag gcc ctc atc tcg ctc ttc       240
Ser Ser Ala Gly Tyr Val Glu Arg Ala Gln Ala Leu Ile Ser Leu Phe
65                  70                  75                  80 acc ctc gag gag ctc att ctc aac acg caa aac tcg ggc ccc ggc gtg       288
Thr Leu Glu Glu Leu Ile Leu Asn Thr Gln Asn Ser Gly Pro Gly Val
                85                  90                  95 cct cgc ctg ggt ctt ccg aac tac caa gtc tgg aat gag gct ctg cac       336
Pro Arg Leu Gly Leu Pro Asn Tyr Gln Val Trp Asn Glu Ala Leu His
            100                 105                 110 ggc ttg gac cgc gcc aac ttc gcc acc aag ggc ggc cag ttc gaa tgg       384
Gly Leu Asp Arg Ala Asn Phe Ala Thr Lys Gly Gly Gln Phe Glu Trp
        115                 120                 125 gcg acc tcg ttc ccc atg ccc atc ctc act acg gcg gcc ctc aac cgc       432
Ala Thr Ser Phe Pro Met Pro Ile Leu Thr Thr Ala Ala Leu Asn Arg
    130                 135                 140 aca ttg atc cac cag att gcc gac atc atc tcg acc caa gct cga gca       480
Thr Leu Ile His Gln Ile Ala Asp Ile Ile Ser Thr Gln Ala Arg Ala
145                 150                 155                 160 ttc agc aac agc ggc cgt tac ggt ctc gac gtc tat gcg cca aac gtc       528
Phe Ser Asn Ser Gly Arg Tyr Gly Leu Asp Val Tyr Ala Pro Asn Val
                165                 170                 175 aat ggc ttc cga agc ccc ctc tgg ggc cgt ggc cag gag acg ccc ggc       576
Asn Gly Phe Arg Ser Pro Leu Trp Gly Arg Gly Gln Glu Thr Pro Gly
            180                 185                 190 gaa gac gcc ttt ttc ctc agc tcc gcc tat act tac gag tac atc acg       624
Glu Asp Ala Phe Phe Leu Ser Ser Ala Tyr Thr Tyr Glu Tyr Ile Thr
        195                 200                 205 ggc atc cag ggt ggc gtc gac cct gag cac ctc aag gtt gcc gcc acg       672
Gly Ile Gln Gly Gly Val Asp Pro Glu His Leu Lys Val Ala Ala Thr
    210                 215                 220 gtg aag cac ttt gcc gga tac gac ctc gag aac tgg aac aac cag tcc       720
Val Lys His Phe Ala Gly Tyr Asp Leu Glu Asn Trp Asn Asn Gln Ser
225                 230                 235                 240 cgt ctc ggt ttc gac gcc atc ata act cag cag gac ctc tcc gaa tac       768
Arg Leu Gly Phe Asp Ala Ile Ile Thr Gln Gln Asp Leu Ser Glu Tyr
                245                 250                 255
```

| | |
|---|---|
| tac act ccc cag ttc ctc gct gcg gcc cgt tat gca aag tca cgc agc<br>Tyr Thr Pro Gln Phe Leu Ala Ala Ala Arg Tyr Ala Lys Ser Arg Ser<br>260 265 270 | 816 |
| ttg atg tgc gca tac aac tcc gtc aac ggc gtg ccc agc tgt gcc aac<br>Leu Met Cys Ala Tyr Asn Ser Val Asn Gly Val Pro Ser Cys Ala Asn<br>275 280 285 | 864 |
| agc ttc ttc ctg cag acg ctt ttg cgc gag agc tgg ggc ttc ccc gaa<br>Ser Phe Phe Leu Gln Thr Leu Leu Arg Glu Ser Trp Gly Phe Pro Glu<br>290 295 300 | 912 |
| tgg gga tac gtc tcg tcc gat tgc gat gcc gtc tac aac gtt ttc aac<br>Trp Gly Tyr Val Ser Ser Asp Cys Asp Ala Val Tyr Asn Val Phe Asn<br>305 310 315 320 | 960 |
| cct cat gac tac gcc agc aac cag tcg tca gcc gcc gcc agc tca ctg<br>Pro His Asp Tyr Ala Ser Asn Gln Ser Ser Ala Ala Ala Ser Ser Leu<br>325 330 335 | 1008 |
| cga gcc ggc acc gat atc gac tgc ggt cag act tac ccg tgg cac ctc<br>Arg Ala Gly Thr Asp Ile Asp Cys Gly Gln Thr Tyr Pro Trp His Leu<br>340 345 350 | 1056 |
| aac gag tcc ttt gtg gcc ggc gaa gtc tcc cgc ggc gag atc gag cgg<br>Asn Glu Ser Phe Val Ala Gly Glu Val Ser Arg Gly Glu Ile Glu Arg<br>355 360 365 | 1104 |
| tcc gtc acc cgt ctg tac gcc aac ctc gtc cgt ctc gga tac ttc gac<br>Ser Val Thr Arg Leu Tyr Ala Asn Leu Val Arg Leu Gly Tyr Phe Asp<br>370 375 380 | 1152 |
| aag aag aac cag tac cgc tcg ctc ggt tgg aag gat gtc gtc aag act<br>Lys Lys Asn Gln Tyr Arg Ser Leu Gly Trp Lys Asp Val Val Lys Thr<br>385 390 395 400 | 1200 |
| gat gcc tgg aac atc tcg tac gag gct gct gtt gag ggc atc gtc ctg<br>Asp Ala Trp Asn Ile Ser Tyr Glu Ala Ala Val Glu Gly Ile Val Leu<br>405 410 415 | 1248 |
| ctc aag aac gat ggc act ctc cct ctg tcc aag aag gtg cgc agc att<br>Leu Lys Asn Asp Gly Thr Leu Pro Leu Ser Lys Lys Val Arg Ser Ile<br>420 425 430 | 1296 |
| gct ctg atc gga cca tgg gcc aat gcc aca acc caa atg caa ggc aac<br>Ala Leu Ile Gly Pro Trp Ala Asn Ala Thr Thr Gln Met Gln Gly Asn<br>435 440 445 | 1344 |
| tac tat ggc cct gcc cca tac ctc atc agc cct ctg gaa gct gct aag<br>Tyr Tyr Gly Pro Ala Pro Tyr Leu Ile Ser Pro Leu Glu Ala Ala Lys<br>450 455 460 | 1392 |
| aag gcc ggc tat cac gtc aac ttt gaa ctc ggc aca gag atc gcc ggc<br>Lys Ala Gly Tyr His Val Asn Phe Glu Leu Gly Thr Glu Ile Ala Gly<br>465 470 475 480 | 1440 |
| aac agc acc act ggc ttt gcc aag gcc att gct gcc gcc aag aag tcg<br>Asn Ser Thr Thr Gly Phe Ala Lys Ala Ile Ala Ala Ala Lys Lys Ser<br>485 490 495 | 1488 |
| gat gcc atc atc tac ctc ggt gga att gac aac acc att gaa cag gag<br>Asp Ala Ile Ile Tyr Leu Gly Gly Ile Asp Asn Thr Ile Glu Gln Glu<br>500 505 510 | 1536 |
| ggc gct gac cgc acg gac att gct tgg ccc ggt aat cag ctg gat ctc<br>Gly Ala Asp Arg Thr Asp Ile Ala Trp Pro Gly Asn Gln Leu Asp Leu<br>515 520 525 | 1584 |
| atc aag cag ctc agc gag gtc ggc aaa ccc ctt gtc gtc ctg caa atg<br>Ile Lys Gln Leu Ser Glu Val Gly Lys Pro Leu Val Val Leu Gln Met<br>530 535 540 | 1632 |
| ggc ggt ggt cag gta gac tca tcc tcg ctc aag agc aac aag aag gtc<br>Gly Gly Gly Gln Val Asp Ser Ser Ser Leu Lys Ser Asn Lys Lys Val<br>545 550 555 560 | 1680 |
| aac tcc ctc gtc tgg ggc gga tat ccc ggc cag tcg gga ggc gtt gcc<br>Asn Ser Leu Val Trp Gly Gly Tyr Pro Gly Gln Ser Gly Gly Val Ala<br>565 570 575 | 1728 |

```
ctc ttc gac att ctc tct ggc aag cgt gct cct gcc ggc cga ctg gtc    1776
Leu Phe Asp Ile Leu Ser Gly Lys Arg Ala Pro Ala Gly Arg Leu Val
        580                 585                 590 acc act cag tac ccg gct gag tat gtt cac caa ttc ccc cag aat gac    1824
Thr Thr Gln Tyr Pro Ala Glu Tyr Val His Gln Phe Pro Gln Asn Asp
    595                 600                 605 atg aac ctc cga ccc gat gga aag tca aac cct gga cag act tac atc    1872
Met Asn Leu Arg Pro Asp Gly Lys Ser Asn Pro Gly Gln Thr Tyr Ile
610                 615                 620 tgg tac acc ggc aaa ccc gtc tac gag ttt ggc agt ggt ctc ttc tac    1920
Trp Tyr Thr Gly Lys Pro Val Tyr Glu Phe Gly Ser Gly Leu Phe Tyr
625                 630                 635                 640 acc acc ttc aag gag act cgc cag cca ccc caa gag cct caa gtt caa    1968
Thr Thr Phe Lys Glu Thr Arg Gln Pro Pro Gln Glu Pro Gln Val Gln
                645                 650                 655 cac ctc atc gat cct ctc tgc tcc tca ccc cgg ata cac tta cag cga    2016
His Leu Ile Asp Pro Leu Cys Ser Ser Pro Arg Ile His Leu Gln Arg
            660                 665                 670 gca gat tcc cgt ctt cac ctt cga ggc caa cat caa gaa ctc ggg caa    2064
Ala Asp Ser Arg Leu His Leu Arg Gly Gln His Gln Glu Leu Gly Gln
        675                 680                 685 gac gga gtc ccc ata tac ggc cat gct gtt tgt tcg cac aag caa cgc    2112
Asp Gly Val Pro Ile Tyr Gly His Ala Val Cys Ser His Lys Gln Arg
    690                 695                 700 tgg ccc agc ccc gta ccc gaa caa gtg gct cgt cgg att cga ccg act    2160
Trp Pro Ser Pro Val Pro Glu Gln Val Ala Arg Arg Ile Arg Pro Thr
705                 710                 715                 720 tgc cga cat caa gcc tgg tca ctc ttc caa gct cag cat ccc cat ccc    2208
Cys Arg His Gln Ala Trp Ser Leu Phe Gln Ala Gln His Pro His Pro
                725                 730                 735 tgt cag tgc tct cgc ccg tgt tga                                    2232
Cys Gln Cys Ser Arg Pro Cys
            740

<210> SEQ ID NO 4
<211> LENGTH: 743
<212> TYPE: PRT
<213> ORGANISM: Trichoderma reesei

<400> SEQUENCE: 4

Met Val Asn Asn Ala Ala Leu Leu Ala Ala Leu Ser Ala Leu Leu Pro
1               5                   10                  15

Thr Ala Leu Ala Gln Asn Asn Gln Thr Tyr Ala Asn Tyr Ser Ala Gln
            20                  25                  30

Gly Gln Pro Asp Leu Tyr Pro Glu Thr Leu Ala Thr Leu Thr Leu Ser
        35                  40                  45

Phe Pro Asp Cys Glu His Gly Pro Leu Lys Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140
```

```
Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205

Gly Ile Gln Gly Gly Val Asp Pro Glu His Leu Lys Val Ala Ala Thr
    210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Arg Tyr Ala Lys Ser Arg Ser
            260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ala Ser Ser Leu
                325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
        355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Lys Lys Ser
                485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Leu Lys Ser Asn Lys Lys Val
545                 550                 555                 560
```

```
Asn Ser Leu Val Trp Gly Gly Tyr Pro Gly Gln Ser Gly Gly Val Ala
            565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile
    610                 615                 620

Trp Tyr Thr Gly Lys Pro Val Tyr Glu Phe Ser Gly Leu Phe Tyr
625                 630                 635                 640

Thr Thr Phe Lys Glu Thr Arg Gln Pro Pro Gln Glu Pro Gln Val Gln
                645                 650                 655

His Leu Ile Asp Pro Leu Cys Ser Ser Pro Arg Ile His Leu Gln Arg
                660                 665                 670

Ala Asp Ser Arg Leu His Leu Arg Gly Gln His Gln Glu Leu Gly Gln
            675                 680                 685

Asp Gly Val Pro Ile Tyr Gly His Ala Val Cys Ser His Lys Gln Arg
        690                 695                 700

Trp Pro Ser Pro Val Pro Glu Gln Val Ala Arg Arg Ile Arg Pro Thr
705                 710                 715                 720

Cys Arg His Gln Ala Trp Ser Leu Phe Gln Ala Gln His Pro His Pro
                725                 730                 735

Cys Gln Cys Ser Arg Pro Cys
            740

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
atggtgaata acgcagctct                                                 20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
cgagtttctg gcgtggttac                                                 20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
actaaaacgt aagctaaacg                                                 20

<210> SEQ ID NO 8
<211> LENGTH: 20
<212> TYPE: DNA
<213> ORGANISM: Artificial Sequence
<220> FEATURE:
<223> OTHER INFORMATION: PCR primer
```

```
<400> SEQUENCE: 8
gcctatccaa tgatgactag                                                  20
```

TRICHODERMA FUNGUS HAVING MUTANT-TYPE BXL1 GENE AND METHOD OF PRODUCING XYLOOLIGOSACCHARIDE AND GLUCOSE BY USING SAME

TECHNICAL FIELD

This disclosure relates to a fungus belonging to the genus *Trichoderma* having a mutant BXL1 gene lacking β-xylosidase (BXL1) activity and a method of producing xylo-oligosaccharides and glucose from a cellulose-based biomass using the same.

BACKGROUND

Xylo-oligosaccharide is a general term of oligosaccharides formed by β-glycosidic linkages of a plurality of xylose units. Xylo-oligosaccharides are also used as a material for functional foods because of, for example, its excellent intestine-regulating function (Aachary A. A. et al., Compre. Rev. Food. Sci. Food Saf. 10, 2-16 (2011)).

Xylo-oligosaccharides can be obtained through hydrolysis of xylan contained in cellulose-based biomass. Known hydrolysis methods include hydrothermal treatment method (Moniz P. et al., Ind. Crops. Prod. 62, 460-465 (2014)), acid hydrolysis method (Akpinar O. et al., Carbohydr. Res. 344, 660-666 (2009)), and enzyme treatment method (JP 4675139 B).

When biomass is to be hydrolyzed with enzymes, filamentous fungi are suitably applied because of their excellent capacity of producing cellulase which is an enzyme that degrades cellulose and xylan. However, it is known that cellulase produced by filamentous fungi degrades xylo-oligosaccharides into monosaccharide xylose in the reaction with biomass. β-xylosidase is known as an enzyme that degrades xylo-oligosaccharides into xylose, and β-xylosidase 1 derived from *Trichoderma reesei* has been reported to react with xylo-oligosaccharides from disaccharide (xylobiose) to heptasaccharide (xyloheptose) to generate xylose (Herrmann M. C. et al., Biochem. J. 321, 375-381 (1997)).

β-xylosidase 1 belongs to glycoside hydrolase family 3 (GH3) (Carbohydrate-Active EnZYmes Database). Enzymes belonging to GH3 comprise a plurality of highly conserved regions (domains), and β-xylosidase 1 of *Trichoderma reesei* comprises N- and C-terminal domains of GH3. In β-xylosidase of *Trichoderma reesei*, amino acid residues at positions 264, 311, and 464 are considered essential for its activity (Rasmussen L. E. et al., Biotech. Bioeng. 94, 5, 869-876 (2006) and Margolles-Clark E. et al., Appl. Environ. Microbiol. 62, 10, 3840-3846 (1996)). Other than these domains, β-xylosidase 1 comprises Fn3-like domain, but the function of Fn3-like domain is not known.

Thus, there is a problem with the use of cellulase of a fungus belonging to the genus *Trichoderma* in that it degrades xylan into xylose.

The Applicant hereby incorporates by reference the sequence listing contained in the ASCII text file titled SequenceListing.txt, created Sep. 26, 2018 and having 35.9 KB of data.

SUMMARY

We found that the use of a fungus belonging to the genus *Trichoderma* in which the amino acid sequence of β-xylosidase 1 comprises the N- and C-terminal domains of GH3 and lacks the Fn3-like domain results in deletion of β-xylosidase activity and increase in β-glucosidase activity.

We thus provide:

(1) A fungus belonging to the genus *Trichoderma* comprising a mutant BXL1 gene encoding mutant β-xylosidase 1 which has N- and C-terminal domains of glycoside hydrolase family 3 (GH3) and lacks Fn3-like domain in β-xylosidase 1 consisting of the amino acid sequence of SEQ ID NO: 2 or in a polypeptide consisting of an amino acid sequence having a sequence identity of 80% or more to the amino acid sequence of SEQ ID NO: 2 and having β-xylosidase activity, the mutant β-xylosidase 1 lacking β-xylosidase activity.

(2) The fungus belonging to the genus *Trichoderma* according to (1), wherein the sequence identity is 95% or more.

(3) The fungus belonging to the genus *Trichoderma* according to (1) or (2), wherein the mutant BXL1 gene encodes a mutant polypeptide having N- and C-terminal domains of GH3, and lacks the Fn3-like domain in the amino acid sequence of SEQ ID NO: 2.

(4) The fungus belonging to the genus *Trichoderma* according to any one of (1) to (3), wherein deletion of the Fn3-like domain is caused by a frame shift by base deletion or insertion, or a stop codon mutation by base substitution, within a gene region encoding a region downstream of the C-terminal domain and upstream of the Fn3-like domain.

(5) The fungus belonging to the genus *Trichoderma* according to any one of (1) to (4), wherein the fungus belonging to the genus *Trichoderma* is a non-recombinant.

(6) The fungus belonging to the genus *Trichoderma* according to any one of (1) to (5), wherein the fungus belonging to the genus *Trichoderma* is *Trichoderma reesei*.

(7) The fungus belonging to the genus *Trichoderma* according to (5), wherein the fungus belonging to the genus *Trichoderma* is a strain in which carbon catabolite repression is removed.

(8) A method of producing a cellulase composition, the method comprising the step of culturing the fungus belonging to the genus *Trichoderma* according to any one of (1) to (7).

(9) A method of producing glucose and xylo-oligosaccharides, the method comprising the steps of: recovering a cellulase composition produced by the method according to (8); and hydrolyzing a biomass containing xylan and cellulose with the obtained cellulase composition.

By using a fungus belonging to the genus *Trichoderma* having a gene encoding mutant β-xylosidase 1 which has N- and C-terminal domains of glycoside hydrolase family 3 (GH3) and lacks Fn3-like domain in β-xylosidase 1, the β-xylosidase activity can be deleted and β-glucosidase activity can be increased. Further, the cellulase composition derived from the fungus belonging to the genus *Trichoderma* can be used for efficient production of glucose and xylo-oligosaccharides.

BRIEF DESCRIPTION OF THE DRAWINGS

FIG. 1 shows a schematic representation of a plasmid construct for insertion of a mutant BXL1 gene, prepared in the Examples below.

DETAILED DESCRIPTION

Our *Trichoderma* fungus and methods are based on the new finding that the β-xylosidase activity can be deleted by using a fungus belonging to the genus *Trichoderma* having a gene encoding mutant BXL1 lacking Fn3-like domain, which is a domain in β-xylosidase of fungus belonging to the genus *Trichoderma* with unknown function.

The fungus belonging to the genus *Trichoderma* is not restricted as long as it has a capacity to produce proteins. Specific examples of the fungi belonging to the genus *Trichoderma* include *Trichoderma virens, Trichoderma harzianum, Trichoderma atroviride, Trichoderma gamsii*, and *Trichoderma reesei*. Among them, preferred is *Trichoderma reesei*. Mutant strains derived from the genus *Trichoderma* and having been subjected to mutagenesis with a mutagen or ultraviolet irradiation to obtain improved protein productivity may also be used. Preferred examples of the mutant strains include known mutant strains derived from *Trichoderma reesei* such as QM6a strain (NBRC31326), QM9414 strain (NBRC31329), PC-3-7 strain (ATCC66589), QM9123 strain (NBRC31327), RutC-30 strain (ATCC56765), CL-847 strain (Enzyme. Microbiol. Technol. 10, 341-346 (1988)), MCG77 strain (Biotechnol. Bioeng. Symp. 8, 89(1978)) and MCG80 strain (Biotechnol. Bioeng. 12, 451-459 (1982)), and derivative strains thereof.

Preferred fungi belonging to the genus *Trichoderma* are those in which carbon catabolite repression is removed. The strains in which carbon catabolite repression is removed can produce more proteins because the production of proteins such as cellulase is elevated. More preferred strains are those in which carbon catabolite repression mediated by carbon catabolite repressor I is removed. The carbon catabolite repression mediated by carbon catabolite repressor I is removed, for example, by a mutation in the carbon catabolite repressor I gene (cre1). It is known that CRE1 protein encoded by cre1 gene suppresses the expression of cellulase gene through catabolite repression by glucose (FEBS Lett., 376, 103-107, 1995). Therefore, when the cre1 gene is mutated, suppression of the expression of the cellulase gene is canceled and the production of cellulase is increased. Therefore, strains with a mutation in cre1 gene are more suitable for producing proteins and cellulase compositions. Specific examples of mutation in the carbon•cre1 gene includes a mutation in the cre1 gene of PC-3-7 strain (ATCC66589), in which A at position 232 is substituted with C, resulting in substitution of threonine at position 78 of the amino acid sequence with proline. It is known that this mutation elevates the production of cellulase (Biosci. Biotechnol. Biochem., 77 (3), 534-543, 2013). It is known that in the RutC-30 strain (ATCC 56765) the cre1 gene is partly cleaved so that the carbon catabolite repression is removed (BMC Genomics., 9, 327, 2008). Strains having a mutation in the cre1 gene include strains having a frame shift by deletion or insertion of a base, a stop codon mutation by base substitution, or a base cleavage within the cre1 gene region, generated by a gene mutating agent, ultraviolet irradiation or the like. Also included are strains in which all or part of the cre1 gene is removed or replaced with another gene by recombination or the like. Specifically, PC-3-7 strain (ATCC66589) and RutC-30 strain (ATCC56765), as well as strains that have inherited the characteristics of PC-3-7 strain (ATCC66589) or RutC-30 strain (ATCC56765) are preferably used, and more preferably PC-3-7 strain (ATCC66589), and strains that have inherited the characteristics of PC-3-7 strain (ATCC66589). The strains that have inherited the characteristics of PC-3-7 (ATCC66589) or RutC-30 strain (ATCC56765) also include those that have inherited the characteristics of PC-3-7 strain (ATCC66589) or RutC-30 strain (ATCC56765) and are newly mutated, and those that have a function improved by recombination.

The amino acid sequence of BXL1 of *Trichoderma reesei* is shown in SEQ ID NO: 2, and the base sequence encoding this amino acid sequence is shown in SEQ ID NO: 1. A gene encoding the amino acid sequence of SEQ ID NO: 2 can be preferably used as an original gene before deletion of Fn3-like domain. A gene encoding a polypeptide consisting of an amino acid sequence having a sequence identity of 80% or more, preferably 85% or more, more preferably 90% or more, still more preferably 93% or more, still more preferably 95% or more, still more preferably 97% or more, still more preferably 99% or more to the amino acid sequence of SEQ ID NO: 2 and having β-xylosidase activity can also be used as the original gene (hereinafter, the amino acid sequence of a polypeptide consisting of an amino acid sequence having a sequence identity of 80% or more to the amino acid sequence of SEQ ID NO: 2 and having β-xylosidase activity is conveniently referred to as "amino acid sequence similar to SEQ ID NO: 2"). The sequence identity between two amino acid sequences represents a percentage determined by aligning the sequences such that the number of matching amino acids is maximized and dividing the number of matching amino acids by the total number of amino acids (by the number of longer amino acids when the total numbers of amino acids are different), and can be easily calculated by using a well-known software such as BLAST. Similarly, the sequence identity between two base sequences represents a percentage determined by aligning the sequences such that the number of matching bases is maximized and dividing the number of matching bases by the total number of bases (by the number of longer bases when the total numbers of bases are different), and can be easily calculated by using a well-known software such as BLAST.

The fungus belonging to the genus *Trichoderma* lacks β-xylosidase activity. β-xylosidase is an enzyme that degrades xylobiose formed by β-1,4-linkage of xylose units to produce xylose. The enzyme activity (U: unit) of β-xylosidase can be measured, for example, by using p-nitrophenyl-β-xylopyranoside (pNP-Xyl) as a substrate. "Lacking the β-xylosidase activity" means that the β-xylosidase activity is reduced to ⅒ or less, more preferably ¹⁄₂₀ or less, still more preferably ¹⁄₅₀ or less, still more preferably ¹⁄₈₀ or less, most preferably ¹⁄₁₀₀ or less, compared to that of parent strain before deleting the FN3-like domain in the BXL1 gene. The activity is calculated as U per mg of protein contained in the enzyme solution.

The lack of β-xylosidase activity is carried out by deletion of the Fn3-like domain in BXL1. In BXL1 consisting of the amino acid sequence of SEQ ID NO: 2, the Fn3-like domain represents the region from 695th to 759th residue in SEQ ID NO: 2. In amino acid sequence similar to SEQ ID NO: 2, the Fn3-like domain represents a region corresponding to the region from 695th to 759th residue in SEQ ID NO: 2. "Corresponding region" refers to the region aligning to the region from 695th to 759th residue in SEQ ID NO: 2 when the amino acid sequence of SEQ ID NO: 2 and the amino acid sequence similar to SEQ ID NO: 2 are aligned such that the number of matching amino acids is maximized. Similarly, in the base sequence of SEQ ID NO: 1, "corresponding region" refers to the region aligning to the region in the base sequence of SEQ ID NO: 1 when the base sequence of SEQ ID NO: 1 and the other base sequence are aligned such that the number of matching bases is maximized. Although the following descriptions are made with respect to the amino acid sequence of SEQ ID NO: 2 representing the amino acid sequence of BXL1 of *Trichoderma reesei* and the base sequence of the gene coding therefor (SEQ ID NO: 1), these descriptions are also applicable to the amino acid sequence similar to SEQ ID NO: 2 and the base sequence of the gene coding therefor. In this case, a specific region within SEQ ID NO: 2 or SEQ ID NO: 1 refers to a corresponding region in the amino acid sequence similar to SEQ ID NO: 2 or in the base sequence coding therefor.

"Deletion of Fn3-like domain" refers to loss of the entire or a part of the domain, change of the entire or a part of the domain into different amino acid(s), or a combination thereof. More specifically, the term means that the sequence identity to the original amino acid sequence of the Fn3-like domain before mutation (SEQ ID NO: 2 or amino acid sequence similar to SEQ ID NO: 2) decreases to 80% or less, preferably to 50% or less, more preferably to 20% or less, still more preferably to 10% or less, still more preferably to 5% or less, still more preferably to 3% or less, still more preferably to 1% or less, most preferably to 0%.

Deletion of the Fn3-like domain is carried out by a mutating treatment with a mutagen, ultraviolet irradiation or the like, or gene recombination. Specifically, the deletion of the Fn3-like domain is caused by a frame shift by base deletion or insertion, or a stop codon mutation by base substitution within a gene region encoding a region upstream of the Fn3-like domain (the region of 1929-2082th bases in the base sequence of BXL1 gene of *Trichoderma reesei* shown in SEQ ID NO: 1) at downstream of the C-terminal domain (described later). Alternatively, the deletion is caused by a frame shift by base deletion or insertion, or a stop codon mutation by base substitution within the base sequence of the Fn3-like domain. On the other hand, the deletion of the Fn3-like domain by gene recombination is achieved such that a part or the entire of amino acids of the Fn3-like domain is lost or changed.

The mutant BXL1 gene has lost the genetic sequence encoding the Fn3-like domain, but has the genetic sequences encoding N- and C-terminal domains of glycoside hydrolase family 3 (GH3). The N-terminal domain of GH3 refers to 84th to 375th residues of BXL1 (SEQ ID NO: 2), and the C-terminal domain of GH3 refers to 414th to 642nd residues of BXL1 (SEQ ID NO: 2). The N- and C-terminal domains of GH3 are considered to be involved in the β-xylosidase activity. The N- and C-terminal regions of GH3 family also comprise the above-described 264th, 311th, and 464th amino acid residues which are considered to be involved in the β-xylosidase activity. "Having a domain" means that the amino acid sequence of the domain does not change at all from SEQ ID NO: 2. Conservation of the Fn3-like domain or N- and C-terminal sequences of GH3 family in the amino acid sequence of β-glucosidase can be confirmed by using an amino acid sequence analysis software "Conserved Domains" provided online by NCBI (The National Center for Biotechnology Information).

A fungus belonging to the genus *Trichoderma* having the mutant BXL1 gene can be obtained by using a gene recombination technique or a non-recombination technique using mutagenesis or the like. Specifically, the fungus belonging to the genus *Trichoderma* having the mutant BXL1 gene can be obtained by: conducting a mutagenesis with NTG treatment or the like; culturing the selected colonies; determining the activity for degrading p-nitrophenyl-β-xylopyranoside; and obtaining the strain having a reduced activity. Non-recombinants can be used for the manufacture more advantageously than recombinants because the containment measures are not necessary, which measures are necessary in case of using a recombinant.

A cellulase composition can be obtained by culturing the fungus belonging to the genus *Trichoderma*. Glucose and xylo-oligosaccharides can be produced by hydrolyzing a biomass containing xylan and cellulose with the obtained cellulase composition.

The cellulase composition is a mixture of various hydrolases that hydrolyze glycosidic linkages within β-1,4-glucans. Examples of hydrolases contained in the cellulase composition include cellobiohydrolase, xylanase, endoglucanase, β-glucosidase, β-xylosidase, arabinofuranosidase, xylanesterase, ferulic acid esterase, α-glucuronidase, chitosanase, chitinase, mannanase, mannosidase, α-galactosidase, and β-galactosidase.

In the cellulase composition obtained, among the above-described hydrolases, the β-xylosidase activity is deleted while the β-glucosidase activity is increased.

β-glucosidase is an enzyme that degrades cellobiose formed by β-1,4-linkage of glucose units to produce glucose. The enzyme activity (U: unit) of β-glucosidase can be measured, for example, by using p-nitrophenyl-β-glucopyranoside (pNP-Glu) as a substrate. "The β-glucosidase activity is increased" means that the β-glucosidase activity is increased by 0.2% or more, more preferably by 0.5% or more, still more preferably by 1% or more, still more preferably by 2% or more compared to that of parent strain before deleting the Fn3-like domain in the BXL1 gene.

The method of culturing the fungus belonging to the genus *Trichoderma* is not restricted as long as the cellulase composition can be produced, including well-known methods of culturing the fungi belonging to the genus *Trichoderma*. A biomass is preferably used as the carbon source contained in the culture medium to be used and as an inducer. As the nitrogen source to be used, for example, polypeptone, bouillon, CSL, soybean cake or the like is used. In addition to these, components required for producing the desired cellulase can be added to the culture medium. For the culture, various culturing methods such as shaking culture, stirring culture, stirring and shaking culture, standing culture, and continuous culture can be employed, and among them, shaking culture and stirring culture are preferred. The culture temperature is usually 20° C. to 35° C., preferably 25° C. to 31° C. The culture time is usually 3 to 10 days, preferably 4 to 9 days.

An inducer may be added to increase the amount of the cellulase composition during culture. The inducer is not restricted and a biomass is preferably used. Biomass is an organic resource derived from a renewable organism. Among various biomass, those containing cellulose and xylan are preferably used. Specific examples of the biomass includes grass biomass such as pulp, bagasse, switchgrass, napier grass, Erianthus, corn stover, corn hull, rice straw, and wheat straw; and woody biomass such as trees, and waste building materials.

These inducers may be treated to be suitable for addition to the culture media. As specific treatment methods, known methods such as acid treatment, sulfuric acid treatment, dilute sulfuric acid treatment, alkali treatment, hydrothermal treatment, subcritical treatment, fine grinding, and steaming can be used.

The xylan content in the biomass as an inducer is not particularly limited, and is preferably at least 5% by weight, more preferably at least 10% by weight, still more preferably at least 20% by weight, based on the solid weight of the biomass. The method of measuring cellulose content and the xylan content in the biomass is not restricted, and specifically the following method can be employed. First, the biomass sample to be measured is air-dried and pulverized with a Wiley mill or the like. After taking an appropriate amount of the sample and drying it at 105° C., the water content (wt %) is calculated from the weight loss. Thereafter, an appropriate amount (about 0.3 g) of the sample is weighed, 3 mL of 72% sulfuric acid is added, and the mixture is allowed to stand at 30° C. for 1 hour with intermittent stirring. The reaction liquid is mixed with 84 mL of purified water and then decomposed by heating in an autoclave at 120° C. for 1 hour. After the thermal decomposition, residues are filtered off from the decomposed liquid. The filtrate and the residue washings are combined to the volume of 100 mL. The monosaccharides (such as glucose and xylose) are quantified by high performance liquid chromatography. The content (cellulose, xylan) in the sample is calculated from the concentration of the obtained monosaccharide (glucose, xylose) and the amount of decomposed sample (dry basis weight calculated from the water content).

The amount of biomass used as an inducer is not particularly limited, and is preferably 5 to 20% by weight, more preferably 8 to 15% by weight, still more preferably 8 to 12% by weight.

The method of using the cellulase composition produced is not restricted, and the cellulase composition may preferably be used in the production of sugars, more preferably in the production of xylo-oligosaccharides, still more preferably in the production of xylo-oligosaccharides and glucose.

"Xylo-oligosaccharides" refer to those formed by β-glycosidic linkage of at least two xylose units. The degree of polymerization of xylo-oligosaccharides is not particularly limited, and preferred are from disaccharide (xylobiose) to hexasaccharide (xylohexaose) having high water solubility. Most preferred xylo-oligosaccharides include xylobiose, xylotriose, and xylotetraose which are easily utilized as carbon sources by enteric bacteria.

The cellulase composition is obtained by culturing the fungus belonging to the genus *Trichoderma*, and used in saccharification reaction of a biomass. The method of preparing the cellulase composition is not restricted, and preferably the cells of the fungus belonging to the genus *Trichoderma* contained in the culture medium are removed, or preferably the fungus belonging to the genus *Trichoderma* does not grow to prevent consumption by the fungal cells of glucose and xylo-oligosaccharides generated by saccharification reaction of cellulase composition and biomass. Examples of the method of removing the fungal cells include centrifugation and membrane separation. The treatment methods of preventing the bacterial cells from growing include heat treatment, chemical treatment, acid/alkali treatment, and UV treatment.

Next, the hydrolysis reaction will be described. The biomass subjected to the hydrolysis reaction is not restricted as long as it is a biomass containing cellulose and xylan, and examples of the biomass include plants such as seed plants, pteridophytes, bryophytes, algae, and water plants, as well as pulp and waste building materials. Seed plants are divided into gymnosperms and angiosperms, both of which can be used preferably. Specific examples of gymnosperms include cycad, ginkgo, pine, fir, spruce, and cryptomeria. Angiosperms are further divided into monocotyledons and dicotyledons. Specific examples of monocotyledons include bagasse, switchgrass, napier grass, Erianthus, corn stover, corncob, rice straw, and wheat straw. Specific examples of dicotyledons used preferably include beet pulp, eucalyptus, oak, and white birch.

The biomass containing cellulose and xylan may be pretreated so that the hydrolysis reaction proceeds easily. The pretreatment method is not restricted and specifically, known methods such as acid treatment, sulfuric acid treatment, dilute sulfuric acid treatment, alkali treatment, hydrothermal treatment, subcritical treatment, fine grinding treatment, and steaming treatment can be used. The reaction pH is not restricted and is preferably about 3 to 7, more preferably 4 to 6, still more preferably about 5. The reaction temperature is not restricted and is preferably 40° C. to 70° C. The amount of the cellulase composition used in the reaction is also not restricted. The reaction time is also not restricted.

The post-reaction liquid produced from the saccharification reaction may contain, in addition to xylo-oligosaccharides and glucose, for example, monosaccharides such as mannose, arabinose, and galactose; and oligosaccharides such as cellobiose, cellotetraose, mannobiose, and galactobiose, which are generated by hydrolases contained in the cellulase composition.

The post-reaction liquid produced from the saccharification reaction may contain, for example, inorganic salts, amino acids, proteins, and lignin as impurities. Purification may be carried out to remove these impurities. As the purification, known techniques such as ion exchange, membrane separation, crystallization, and demineralization can be employed.

A fraction containing monosaccharides (such as glucose, and xylose) and a fraction containing xylo-oligosaccharides and so on produced are preferably separated in a post-process. Glucose is preferably used as a fermentation raw material in the production of chemical products, while xylo-oligosaccharides are preferably used for feeds, foods and cosmetic applications. Specific examples of the chemical products include alcohols such as ethanol, 1,3-propanediol, 1,4-butanediol, and glycerol; organic acids such as acetic acid, lactic acid, pyruvic acid, succinic acid, malic acid, itaconic acid, and citric acid; nucleosides such as inosine and guanosine; nucleotides such as inosinic acid and guanylic acid; and amine compounds such as cadaverine.

EXAMPLES

Our fungus and methods will now be described in detail with reference to the Examples. However, this disclosure is not limited to them.

Reference Example 1 Method of Measuring Protein Concentration

A commercially available reagent for measuring protein concentration (Quick Start Bradford protein assay, Bio-Rad) was used. Five microliters of a diluted filamentous fungus-derived cellulase solution was added to 250 μL of the protein concentration measurement reagent which was previously returned to room temperature. After leaving the mixture to stand at room temperature for 5 minutes, the absorbance at 595 nm was measured using a microplate reader. Using BSA as a standard, the protein concentration was calculated based on the calibration curve.

Reference Example 2 Method of Measuring β-Xylosidase Activity

The specific method of measuring β-xylosidase activity was as follows. To 90 μL of 50 mM acetate buffer containing 1 mM p-nitrophenyl-β-xylopyranoside (Sigma-Aldrich Japan), was added 10 μL of enzyme dilution, and the mixture was allowed to react at 30° C. for 30 minutes. Then, 10 μL of 2 M sodium carbonate was added and mixed well to stop the reaction, and the increase in absorbance at 405 nm was determined. Release of 1 μmol of p-nitrophenol per minute was defined as 1 U of activity. For blanks, to 90 μL of 50 mM acetate buffer containing 1 mM p-nitrophenyl-β-xylopyranoside, was added 10 μL of 2 M sodium carbonate and mixed well. Then, 10 μL of enzyme dilution was added to the mixture and allowed to react at 30° C. for 30 minutes. Then, the increase in absorbance at 405 nm was determined.

Reference Example 3 Method of Measuring β-Glucosidase Activity

The specific method of determining β-glucosidase activity was as follows. To 90 μL of 50 mM acetate buffer containing 1 mM p-nitrophenyl-β-glucopyranoside (Sigma-Aldrich Japan), was added 10 μL of enzyme dilution, and the mixture was allowed to react at 30° C. for 10 minutes. Then, 10 μL of 2 M sodium carbonate was added and mixed well to stop the reaction, and the increase in absorbance at 405 nm was determined. Release of 1 μmol of p-nitrophenol per minute was defined as 1 U of activity. For blanks, to 90 μL of 50 mM acetate buffer containing 1 mM p-nitrophenyl-β-glucopyranoside, was added 10 μL of 2 M sodium carbonate and mixed well. Then, 10 μL of enzyme dilution was added to the mixture and allowed to react at 30° C. for 30 minutes. Then, the increase in absorbance at 405 nm was determined.

Reference Example 4 Method of Measuring Cellobiohydrolase Activity

The specific method of measuring cellobiohydrolase activity was as follows. To 90 μL of 50 mM acetate buffer containing 1 mM p-nitrophenyl-β-lactopyranoside (Sigma-Aldrich Japan), was added 10 μL of enzyme dilution, and the mixture was allowed to react at 30° C. for 60 minutes. Then, 10 μL of 2 M sodium carbonate was added and mixed well to stop the reaction, and the increase in absorbance at 405 nm was determined. Release of 1 μmol of p-nitrophenol per minute was defined as 1 U of activity. For blanks, to 90 μL of 50 mM acetate buffer containing 1 mM p-nitrophenyl-β-lactopyranoside, was added 10 μL of 2 M sodium carbonate and mixed well. Then, 10 μL of enzyme dilution was added to the mixture and allowed to react at 30° C. for 30 minutes. Then, the increase in absorbance at 405 nm was determined.

Reference Example 5 Measurement of Sugar Concentration

Quantitative analysis of xylo-oligosaccharide, glucose, and xylose was carried out using LaChrom Eite high performance liquid chromatography (HITACHI) under the following conditions.

The quantitative analyses were based on calibration curves prepared with standards of xylobiose, xylotriose, xylotetraose, xylopentaose, and xylohexaose which are xylo-oligosaccharides, and with glucose and xylose standards. The xylo-oligosaccharides described in this example refer to xylo-oligosaccharides in which 2 to 6 xylose units are bound by β-glycosidic bonds.

Column: KS802, KS803 (Shodex)
Mobile phase: water
Detection method: RI
Flow rate: 0.5 mL/min
Temperature: 75° C.

Comparative Example 1 Preparation of BXL1 Gene-Disrupted Recombinant *Trichoderma reesei* PC-3-7 Strain A non-limiting method of disrupting a gene of interest by homologous recombination comprises: carrying out PCR using primers designed to add portions homologous to the introduction target site, to upstream and downstream of the DNA containing a marker gene; and transforming a filamentous fungus with the obtained PCR fragments.

The transformation was carried out by a standard method (PEG-mediated protoplast transformation). The host used was PC-3-7 strain, and the marker used was acetamidase (AmdS) gene.

Introduction of AmdS gene into the obtained transformant was confirmed by culturing the transformant in PDA medium; extracting genomic DNA from the transformant; and carrying out PCR using the extract as the template. PDA medium contained 24 g/L Difco Potato Dextrose Broth (BD) as an ingredient. From the result, substitution of BXL1 gene with AmdS gene cassette in the transformant was confirmed. The PC-3-7 strain in which AmdS gene cassette was introduced into BXL1 locus, obtained from the above step, is hereinafter referred to as PC-3-7/ΔBXL1 strain. The strain had lost all three domains in the ORF of the BXL1 gene.

Example 1 Preparation of *Trichoderma reesei* PC-3-7 Strain Having Gene Encoding Mutant BXL1

The base sequence of SEQ ID NO: 3 was used as the mutant BXL1 gene. The mutant BXL1 gene had lost the base sequence of 1940th and 1941th bases in the BXL1 gene of *Trichoderma reesei* (SEQ ID NO: 1), thus having a frame-shift in the subsequent amino acid sequence. The homology between the amino acid sequence encoded by the mutant BXL1 gene and the amino acid sequence of Fn3-like domain of SEQ ID NO: 2 was 0%. The mutant BXL1 gene was prepared by artificial synthesis.

A non-limiting method of inserting a DNA containing the mutant BXL1 gene into downstream of the promoter of BXL1 in a chromosome by homologous recombination comprises: carrying out PCR using primers designed to add portions homologous to the introduction target site, to upstream and downstream of the DNA containing mutant BXL1 gene; and transforming a filamentous fungus with the obtained PCR fragments.

The transformation was carried out by a standard method (PEG-mediated protoplast transformation). The host used was PC-3-7 strain, and the marker used was acetamidase (AmdS) gene. FIG. 1 shows the plasmid for insertion of the mutant BXL1 gene prepared by molecular biological technique. The plasmid contained the mutant BXL1 gene (SEQ ID NO: 3) followed by 500 bp region downstream from the stop codon of the BXL1 gene. Further, the plasmid also contained the acetamidase gene cassette and a gene sequence homologous to the region from 501 bp to about 2.5 kb downstream of the BXL1 gene. Using the plasmid, the mutant BXL1 gene insertion cassette was amplified by PCR, and the amplified products were used for recombination. More specifically, transformation was carried out as described in Gene, 61, 165-176 (1987). The amplification of the mutant BXL1 gene insertion cassette was carried out by PCR using the designed primers (SEQ ID NOS: 5 and 6).

Introduction of the gene of interest into the obtained transformant was confirmed by culturing the transformant in PDA medium; extracting genomic DNA from the transformant; and carrying out PCR using the extract as the template. Specifically, designed primers (SEQ ID NOS: 7 and 8) were used for the confirmation. From the result, introduction of the mutant BXL1 gene cassette from the start codon of the BXL1 gene was confirmed in the transformant. The obtained PC-3-7 strain is hereinafter referred to as PC-3-7/mutant BXL1 strain.

Comparative Example 2 Preparation of Cellulase Composition Derived from *Trichoderma reesei* PC-3-7 Strain Preculture Spores of *Trichoderma reesei* strain PC-3-7 were suspended in physiological saline to $1.0 \times 10^7$/mL, and 2.5 mL of the spore suspension was inoculated into 250 mL of a preculture medium having the composition described in Table 1 and placed in a 1 L baffled flask. The inoculated preculture medium was incubated at 28° C. and 160 rpm for 3 days.

TABLE 1

| Components | per 1 L |
| --- | --- |
| D-glucose | 20 g |
| 5× Mandel's medium** | 200 mL |
| 10× ammonium tartrate | 100 mL |
| corn steep liquor | 15 g |
| trace element * | 1 mL |
| Tween 80 | 0.5 mL |
| antifoaming agent (PE-M) | 1 mL |

* The trace element solution contains 0.3 g/L $H_3BO_3$, 1.3 g/L $(NH_4)_6Mo_7O_{24} \cdot 4H_2O$, 5 g/L $FeCl_3 \cdot 6H_2O$, 2 g/L $CuSO_4 \cdot 5H_2O$, 0.4 g/L $MnCl_2 \cdot 4H_2O$, and 10 g/L $ZnCl_2$.
**The Mandel's medium contains 7 g/L $(NH_4)_2SO_4$, 10 g/L $KH_2PO_4$, 3 g/L $CaCl_2$, and 3 g/L $MgSO_4 \cdot 7H_2O$.

Main Culture

The preculture of *Trichoderma reesei* strain PC-3-7 in an amount of 250 mL were each inoculated into 2.5 L of the main culture medium (further containing 250 g of biomass) shown in Table 2 and placed in a 5 L mini jar. The inoculum was cultured at 28° C., 700 rpm, 1 vvm, pH5, for 5 days. Neutralization was performed with 10% ammonia and 1 N sulfuric acid. ARBOCEL (registered trademark) (J. Rettenmaier & Sohne) was used as the biomass.

TABLE 2

| Components | per 1 L |
| --- | --- |
| ARBOCEL (registered trademark)*** (J. Rettenmaier&Sohne) | 100 g |
| 5× Mandel's medium** | 200 mL |
| corn steep liquor | 25 g |
| trace element* | 1 mL |
| Tween 80 | 0.5 mL |
| antifoaming agent (PE-M) | 1 mL |

*The trace element solution contains 0.3 g/L $H_3BO_3$, 1.3 g/L $(NH_4)_6Mo_7O_{24} \cdot 4H_2O$, 5 g/L $FeCl_3 \cdot 6H_2O$, 2 g/L $CuSO_4 \cdot 5H_2O$, 0.4 g/L $MnCl_2 \cdot 4H_2O$, and 10 g/L $ZnCl_2$.
**The Mandel's medium contains 7 g/L $(NH_4)_2SO_4$, 10 g/L $KH_2PO_4$, 3 g/L $CaCl_2$, and 3 g/L $MgSO_4 \cdot 7H_2O$.
***ARBOCEL is mixed with other components and diluted in a measuring cylinder before addition.

Culture Collection

Every three days from the start of culture, 500 μL of the culture was collected. The culture was centrifuged at 15,000×g, 4° C. for 10 minutes to obtain a supernatant. The supernatant was filtered through a 0.22 μm filter, and the filtrate was used as a culture supernatant. For enzyme activity measurement and saccharification reaction, the culture supernatant on day 5 of culture was used (Table 3).

TABLE 3

| | Comparative Example 2 | Comparative Example 3 | Example 2 |
| --- | --- | --- | --- |
| strain used | PC-3-7 | PC-3-7/ΔBXL1 | PC-3-7/mutant BXL1 |
| β-xylosidase activity (U/mg protein) | 0.400 | 0.002 | 0.002 |
| β-glucosidase activity (U/mg protein) | 0.420 | 0.520 | 0.530 |
| cellobiohydrolase activity (U/mg protein) | 0.158 | 0.159 | 0.159 |

Comparative Example 3 Preparation of Cellulase Composition Derived from *Trichoderma reesei* PC-3-7/ΔBXL1 Strain Preparation was carried out in the same manner as in Comparative Example 2 except that *Trichoderma reesei* PC-3-7/ΔBXL1 strain was used. For enzyme activity measurement and saccharification reaction, the culture supernatant on day 5 of culture was used (Table 3). The results show that the β-xylosidase activity was markedly decreased compared to that with parent PC-3-7 strain.

Example 2 Preparation of Cellulase Composition Derived from *Trichoderma reesei* PC-3-7/Mutant BXL1 Strain Preparation was carried out in the same manner as in Comparative Example 2 except that *Trichoderma reesei* PC-3-7/mutant BXL1 strain was used. For enzyme activity measurement and saccharification reaction, the culture supernatant on day 5 of culture was used (Table 3). The results show that the β-xylosidase activity was decreased to the same level as *Trichoderma reesei* PC-3-7/ΔBXL1 strain. Further, we found that the β-glucosidase activity was increased compared to that with *Trichoderma reesei* PC-3-7/ΔBXL1 strain.

Comparative Example 4 Production of Xylo-Oligosaccharides and Glucose Through Saccharification Reaction Using Cellulase Composition Derived from *Trichoderma reesei* PC-3-7 Strain The filtrate obtained in Comparative Example 2 was used for saccharification. The bagasse used in saccharification reaction had been subjected to alkali treatment (pretreatment). The saccharification reaction was carried out as follows. After 50 mg by dry weight of the alkali-treated bagasse was placed in a 2 mL tube, pure water was added so that the solid content concentration of the bagasse at the start of reaction was 5% by weight, while pH was adjusted to 5.0 with diluted hydrochloric acid. To the pretreatment product with the adjusted pH, was added a cellulase composition to 8 mg/g-biomass, and then the reaction was initiated under reaction conditions of pH 5.0 and at 50° C. using a heat block rotator. During the reaction, the pH was appropriately adjusted to 5. After 8 hours, the reaction mixture was immersed in a water bath at 99° C. for 5 minutes to stop the reaction. The reaction liquid was centrifuged at 8,000×g for 5 minutes to obtain a supernatant. The supernatant was filtered through a 0.22 μm filter, and the filtrate was used for analyses of xylo-oligosaccharides and glucose according to Reference Example 5 (Table 4).

TABLE 4

|  | Comparative Example 4 | Comparative Example 5 | Example 3 |
|---|---|---|---|
| strain used | PC-3-7 | PC-3-7/ΔBXL1 | PC-3-7/mutant BXL1 |
| total xylo-oligosaccharides (g/L) | 0.8 | 6.9 | 6.9 |
| glucose (g/L) | 9.2 | 10.3 | 11.0 |

Comparative Example 5 Production of Xylo-Oligosaccharides and Glucose Through Saccharification Reaction Using Cellulase Composition Derived from *Trichoderma reesei* PC-3-7/ΔBXL1 Strain The filtrate obtained in Comparative Example 3 was used for saccharification. The saccharification reaction was carried out in the same manner as in Comparative Example 4 (Table 4). The results show that the yield of xylo-oligosaccharides was markedly increased compared to the parent PC-3-7 strain.

Example 3 Production of Xylo-Oligosaccharides and Glucose Through Saccharification Reaction Using Cellulase Composition Derived from *Trichoderma reesei* PC-3-7/Mutant BXL1

The saccharification reaction was carried out using the filtrate obtained in Example 2 in the same manner as in Comparative Example 4 (Table 4). The results show that xylo-oligosaccharides yield comparable to that of the filtrate obtained with *Trichoderma reesei* PC-3-7/ΔBXL1 strain was achieved, and also the glucose yield was increased.

INDUSTRIAL APPLICABILITY

The β-xylosidase activity can be lost via deletion of Fn3-like domain from the BXL1 gene. Furthermore, the β-glucosidase activity is increased compared to that with a strain in which all three domains in the BXL1 gene are disrupted, thus enabling efficient production of xylo-oligosaccharides and glucose.

---

The invention claimed is:

1. A fungus belonging to genus *Trichoderma* comprising a mutant BXL1 gene encoding mutant β-xylosidase 1 having N- and C-terminal domains of glycoside hydrolase family 3 (GH3) and lacking Fn3-like domain in β-xylosidase 1 consisting of the amino acid sequence of SEQ ID NO: 2 or in a polypeptide consisting of an amino acid sequence having a sequence identity of 80% or more to the amino acid sequence of SEQ ID NO: 2 and having β-xylosidase activity, said mutant β-xylosidase 1 lacking β-xylosidase activity.

2. The fungus belonging to the genus *Trichoderma* according to claim 1, wherein said sequence identity is 95% or more.

3. The fungus belonging to the genus *Trichoderma* according to claim 1, wherein said mutant BXL1 gene encodes a mutant polypeptide having N- and C-terminal domains of GH3, and lacks the Fn3-like domain in the amino acid sequence of SEQ ID NO: 2.

4. The fungus belonging to the genus *Trichoderma* according to claim 1, wherein deletion of said Fn3-like domain is caused by a frame shift by base deletion or insertion, or a stop codon mutation by base substitution, within a gene region encoding a region downstream of said C-terminal domain and upstream of said Fn3-like domain.

5. The fungus belonging to the genus *Trichoderma* according to claim 1, wherein said fungus belonging to the genus *Trichoderma* is a non-recombinant.

6. The fungus belonging to the genus *Trichoderma* according to claim 1, wherein said fungus belonging to the genus *Trichoderma* is *Trichoderma reesei*.

7. The fungus belonging to the genus *Trichoderma* according to claim 5, wherein said fungus belonging to the genus *Trichoderma* is a strain in which carbon catabolite repression is removed.

8. The fungus belonging to the genus *Trichoderma* according to claim 2, wherein said mutant BXL1 gene encodes a mutant polypeptide having N- and C-terminal domains of GH3, and lacks the Fn3-like domain in the amino acid sequence of SEQ ID NO: 2.

9. The fungus belonging to the genus *Trichoderma* according to claim 2, wherein deletion of said Fn3-like domain is caused by a frame shift by base deletion or insertion, or a stop codon mutation by base substitution, within a gene region encoding a region downstream of said C-terminal domain and upstream of said Fn3-like domain.

10. The fungus belonging to the genus *Trichoderma* according to claim 3, wherein deletion of said Fn3-like domain is caused by a frame shift by base deletion or insertion, or a stop codon mutation by base substitution, within a gene region encoding a region downstream of said C-terminal domain and upstream of said Fn3-like domain.

11. The fungus belonging to the genus *Trichoderma* according to claim 2, wherein said fungus belonging to the genus *Trichoderma* is a non-recombinant.

12. The fungus belonging to the genus *Trichoderma* according to claim 3, wherein said fungus belonging to the genus *Trichoderma* is a non-recombinant.

13. The fungus belonging to the genus *Trichoderma* according to claim 4, wherein said fungus belonging to the genus *Trichoderma* is a non-recombinant.

14. The fungus belonging to the genus *Trichoderma* according to claim 2, wherein said fungus belonging to the genus *Trichoderma* is *Trichoderma reesei*.

15. The fungus belonging to the genus *Trichoderma* according to claim 3, wherein said fungus belonging to the genus *Trichoderma* is *Trichoderma reesei*.

16. The fungus belonging to the genus *Trichoderma* according to claim 4, wherein said fungus belonging to the genus *Trichoderma* is *Trichoderma reesei*.

17. The fungus belonging to the genus *Trichoderma* according to claim 5, wherein said fungus belonging to the genus *Trichoderma* is *Trichoderma reesei*.

18. A method of producing a cellulase composition, said method comprising the step of culturing the fungus belonging to the genus *Trichoderma* according to claim 1.

19. A method of producing glucose and xylo-oligosaccharides, said method comprising the steps of: recovering a cellulase composition produced by the method according to claim 18; and hydrolyzing a biomass containing xylan and cellulose with the obtained cellulase composition.

\* \* \* \* \*